(12) United States Patent
Fu

(10) Patent No.: US 7,044,737 B2
(45) Date of Patent: May 16, 2006

(54) ULTRASOUND ORAL HYGIENE AND THERAPEUTIC DEVICE

(76) Inventor: Liang Fu, 12046 Gatewater Dr., Potomac, MD (US) 20854

( * ) Notice: Subject to any disclaimer, the term of this patent is extended or adjusted under 35 U.S.C. 154(b) by 8 days.

(21) Appl. No.: 10/792,736

(22) Filed: Mar. 5, 2004

(65) Prior Publication Data
US 2005/0196725 A1 Sep. 8, 2005

(51) Int. Cl.
*A61C 1/07* (2006.01)

(52) U.S. Cl. ....................................... 433/119

(58) Field of Classification Search ................ 433/119, 433/120, 118, 121, 122, 123, 124; 132/322; 15/22.1, 22.2; 601/142, 161
See application file for complete search history.

(56) References Cited

U.S. PATENT DOCUMENTS

| | | | |
|---|---|---|---|
| 3,227,158 A | 1/1966 | Mattingly | |
| 3,380,446 A * | 4/1968 | Martin | ............ 601/2 |
| 3,522,801 A | 8/1970 | Robinson | |
| 3,535,726 A | 10/1970 | Sawyer | |
| 4,011,616 A * | 3/1977 | Kennedy | ................ 15/21.1 |
| 4,071,956 A | 2/1978 | Andress | |
| 4,127,125 A * | 11/1978 | Takemoto et al. | ........... 604/22 |
| 4,148,309 A | 4/1979 | Reibel | |
| 4,176,454 A | 12/1979 | Hatter et al. | |
| 4,223,417 A | 9/1980 | Solow | |
| 4,224,710 A | 9/1980 | Solow | |
| 4,237,574 A | 12/1980 | Kelly et al. | |
| 4,333,197 A | 6/1982 | Kuris | |
| 4,336,622 A | 6/1982 | Teaque, Jr. et al. | |
| 4,787,847 A | 11/1988 | Martin et al. | |
| 4,795,347 A | 1/1989 | Maurer | |
| 4,894,880 A | 1/1990 | Aznavoorian | |
| 4,991,249 A | 2/1991 | Suroff | |
| 5,077,855 A | 1/1992 | Ambasz | |
| 5,146,642 A | 9/1992 | Mank et al. | |
| 5,177,827 A | 1/1993 | Ellison | |
| 5,311,632 A | 5/1994 | Center | |
| 5,353,460 A | 10/1994 | Bauman | |
| 5,378,153 A | 1/1995 | Giuliani et al. | |
| 5,383,242 A | 1/1995 | Bigler et al. | |
| 5,524,312 A | 6/1996 | Tan et al. | |
| 5,546,624 A | 8/1996 | Bock | |
| 5,699,575 A | 12/1997 | Peifer | |
| 5,836,030 A | 11/1998 | Hazeu et al. | |
| 5,894,453 A | 4/1999 | Pond | |
| 5,934,908 A | 8/1999 | Woog et al. | |
| 5,974,615 A | 11/1999 | Schwarz-Hartmann et al. | |
| 6,106,294 A | 8/2000 | Daniel | |
| 6,138,310 A | 10/2000 | Porper et al. | |
| 6,174,164 B1 * | 1/2001 | Masjedi | ................ 433/80 |
| 6,202,241 B1 | 3/2001 | Hassell et al. | |
| 6,209,164 B1 | 4/2001 | Sato | |

(Continued)

*Primary Examiner*—Cary E. O'Connor

(57) ABSTRACT

An ultrasound oral hygiene and therapeutic device comprises an array of ultrasonic transducers, a power generator, and a filling element. The ultrasonic transducer array, with optional radiation plates and reflection plates, produce uniform ultrasound radiation on each surface desirable to be treated by ultrasound radiation. The soft and resilient filling element snugly fits into a user's oral cavity, confines cleaning solution and the ultrasound action within a limited ultrasound action zone surrounding the surfaces desirable to be treated, and protects all other parts of the oral cavity from ultrasound radiation. The device provides superior, uniform, and consistent cleaning results in a short time. In particular, it cleans the entire dental surface, including the inter-dental and gingival areas. It is extremely easy to use, quiet, durable, energy efficient, and inexpensive in long run.

20 Claims, 5 Drawing Sheets

U.S. PATENT DOCUMENTS

| | | | |
|---|---|---|---|
| 6,353,956 B1 * | 3/2002 | Berge | 15/22.1 |
| 6,453,498 B1 | 9/2002 | Wu | |
| 6,514,077 B1 | 2/2003 | Wilk | |
| 2004/0128777 A1 * | 7/2004 | Koh | 15/22.1 |

* cited by examiner

ULTRASOUND ORAL HYGIENE AND THERAPEUTIC DEVICE

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

1. Field of Invention

This invention relates to oral hygiene and therapeutic devices, especially to ultrasound oral hygiene and therapeutic devices.

2. Description of Prior Art

Presently the most popular personal dental cleaning device is still the traditional manual toothbrush. Although it has a long history and has been constantly improved, manual toothbrush suffers from a number of disadvantages:

1. It produces uneven result, more brushing on prominent and easy-to-reach areas and less brushing on depressed and hard-to-reach areas.

2. It does not clean areas that are inaccessible to brush bristles such as inter-dental and gingival areas.

3. It inherently involves a low brushing frequency.

4. It cleans a small area at a time, hence, it is time consuming and a user has to brush over the entire dental surface.

5. It is difficult to provide just the right amount of brushing.

6. It is difficult to brush along the direction of tooth crevices as recommended.

7. It is difficult to maintain just the right pressure.

8. It requires some dexterity from users, which is not typically the case for children or many handicapped adults.

9. It produces inconsistent results for different users and at different times for the same user.

10. The bristles and the abrasive particles in dentifrice can damage the dental surface and the gums if not used correctly.

11. Users have to move their hands vigorously, and such motion can cause muscle fatigue and stress.

12. The bristle tips wear out, hence, the cleaning results deteriorate quickly and the toothbrush has to be replaced regularly.

13. Other supplemental cleaning devices, such as dental floss, are needed.

The major challenge for dental cleaning is the imperfection and randomness of dental surface. The present remedy for this problem is to use bristles of different lengths, as suggested in U.S. Pat. No. 6,202,241 to Hassell et al. (2001) and U.S. Pat. No. 4,894,880 to Aznavoorian (1990) for example. However, since the contours of dental surfaces are so diverse from one individual to another, and from one area to another for the same individual, the result is hardly satisfactory. From this point of view alone, a smaller brush head works better. But a smaller brush head would worsen several other disadvantages listed above, especially disadvantage number 4. Some "whole-mouth" toothbrushes and "U"-shaped three-head toothbrushes have been proposed in attempt to remedy disadvantage number 4. For example, U.S. Pat. No. 4,237,574 to Kelly et al. (1980), U.S. Pat. No. 4,223,417 to Solow (1980), and U.S. Pat. No. 4,795,347 to Maurer (1989). Unfortunately, these designs do not provide satisfactory results as hoped and are difficult to use.

Another major challenge for dental cleaning is that there are areas inaccessible to bristles, such as inter-dental and gingival areas. Presently, supplemental cleaning devices, such as dental floss, toothpicks or the like, are required for cleaning the inter-dental areas. However, these devices can only be used in places that are directly accessible from the outside and are not effective in removing plaque. Furthermore, a user has to work in each tooth crevice, which is time and labor consuming. Another supplemental device for cleaning inter-dental and gingival areas is the high-pressure water jet. Examples of patents include U.S. Pat. No. 3,227,158 to Mattingly (1966) and U.S. Pat. No. 3,522,801 to Robinson (1970). Similar to dental floss, using a high-pressure water jet device is also time and labor consuming, and it is not very effective in removing plaque. In addition, high-pressure water jet irritates gums and may cause bleeding and damage.

Although the recommended brushing time is two minutes, people on average spend less than one minute. To control the time of a brushing session, it has been suggested to equip a timer on a toothbrush, for example, U.S. Pat. No. 6,106,294 to Daniel (2000) and U.S. Pat. No. 5,894,453 to Pond (1999). But a timer can only control the total time of a brushing session. Unless the user can uniformly distribute the preset total time, a timer is not very effective.

In the last few years, the electrical toothbrush began to gain popularity. The dominant group of electrical toothbrushes, which will be referred as ordinary electrical toothbrushes, consists of an electrical motor that produce rotational or vibrational motion, a brush head with bristles, and a mechanical transmission system to transmit the motion of the electrical motor to the brush head, while converting the original motion type of the electrical motor to the final motion type of the brush head.

In order to obtain the desired motion of the brush head, most of the prior-art designs have used rather complicated mechanical transmission systems involving many moving parts, especially those with complex motion type or with a multi-sectional brush head. Referring to a typical ordinary electrical toothbrush that is currently being sold on the market as an example, there is a transmission system that firstly converts the rotational motion of the electrical motor into a longitudinal back and forth motion of a driving shaft, and then converts this longitudinal back and forth motion into a reciprocal rotation of the brush head about an axis perpendicular to the shaft. Complex mechanical systems are inherently unreliable, costly, energy inefficient, and produce discomforting noise. There are hundreds of patents on ordinary electrical toothbrushes and several different types are being sold on the market currently.

The following are some examples of patents categorized by brush head motion types. U.S. Pat. No. 5,699,575 to Peifer (1997) and U.S. Pat. No. 5,146,642 to Mank et al. (1992) provide designs where the brush head rotates about the longitudinal axis of the brush shaft. U.S. Pat. No. 5,836,030 to Hazeu et al. (1998) and U.S. Pat. No. 5,383,242 to Bigler et al. (1995) provide designs where the circular brush head rotate reciprocally about its central axis. U.S. Pat. No. 5,934,908 to Woog et al. (1999) provides a design where the brush head rotates reciprocally about the longitudinal axis. U.S. Pat. No. 5,077,855 to Ambasz (1992) provides a design where the brush head vibrates along the longitudinal axis. U.S. Pat. No. 6,453,498 to Wu (2002) and U.S. Pat. No. 5,378,153 to Giuliani et al. (1995) provide designs where the brush head vibrates sideways. U.S. Pat. No. 4,336,622 to Teague Jr. et al. (1982), U.S. Pat. No. 4,787,847 to Martin et al. (1988), and U.S. Pat. No. 3,535,726 to Sawyer (1970) provide designs where the brush head strokes up and down. U.S. Pat. No. 5,974,615 to Schwarz-Hartmann et al. (1999) provides a design where the circular brush head rotates reciprocally about its central axis, as well as strokes up and down. U.S. Pat. No. 5,353,460 to Bauman (1994) and U.S. Pat. No. 5,524,312 to Tan et al. (1996) provide designs where the brush head has two sections, each of them having its own motion type.

Each of these particular motion types may be suitable for particular sections of dental surface, but none of them alone provides satisfactory results for the entire dental surface. The combined motion or multi-sectional designs may produce better results than single motion types. However, similarly to using bristles of different lengths, the improvement is rather limited. Some of the prior-art designs can detect excessive pressure exerted by the user and either send a warning signal or shut down the power. This provides some guidance and assistance, but it still relies on the user to make the necessary adjustments to maintain the right pressure.

Compared to manual toothbrushes, the most significant improvement that ordinary electrical toothbrushes bring about is the much greater brushing frequency. The fastest model currently sold on the market has a frequency of 500 Hz. This substantially overcomes the low brushing frequency disadvantage (number 3) of the manual toothbrush.

There are also powered versions of the whole-mouth toothbrushes or multi-head toothbrushes. Such as U.S. Pat. No. 5,177,827 to Ellison (1993), U.S. Pat. No. 4,224,710 to Solow (1980), U.S. Pat. No. 6,209,164 to Sato (2001), and U.S. Pat. No. 6,138,310 to Porper et al. (2000). Like their manual counterparts, they are not effective and rather difficult to use. Furthermore, they require very complex mechanical systems.

If all the best parts of the prior-art designs of the ordinary electrical toothbrush were combined, the result would overcome the disadvantages number 3 and 11, and improve to some extent on disadvantages number 1, 5, 6, 7 and 8. All the rest disadvantages of manual toothbrushes (2, 4, 9, 10, 12, and 13) would largely remain unresolved. Furthermore, the ordinary electrical toothbrushes suffer from a number of additional disadvantages of their own:

1. They consist of many moving mechanical parts, which often result in low reliability and high manufacture cost.
2. Brush heads are rather expensive, and they involve substantial cost in long run.
3. They produce discomforting noise.
4. Their mechanical transmission systems are energy inefficient, and the moving parts suffer from considerable friction, since they constantly undergo a stop-and-go (or forward-and-reverse) type of motion.

Ordinary electrical toothbrushes sometimes are referred as sonic electrical toothbrushes. It should be made clear that this simply means that they operate in the audible frequency range. The patents and product commercials of some ordinary electrical toothbrushes claim to have a "sonic wave" effect or even a "cavitation" effect, supposedly capable of cleaning areas that cannot be reached by the bristles, such as inter-dental and gingival areas. That should be more carefully considered, because, according to basic physical principles, ordinary electrical toothbrushes can hardly produce a sonic wave with adequate cleaning power, let alone any cavitation effect.

Acoustic waves in a liquid consist of alternating local compressions and dilatations. First of all, the brush bristle is very inefficient in converting mechanical vibration energy into acoustic wave energy, since it is too weak to significantly compress the liquid. Secondly, in typical tooth brushing there is only a thin layer of loose liquid bounded only by its surface tension. A sufficient degree of compression, or, more technically, acoustic pressure can hardly be produced in such a thin layer of loose liquid at low frequencies (e.g., 500 Hz), since the liquid by and large escapes compression by moving sideways. Thirdly, the bristles stir air into the thin layer of liquid making it into a foam form, which is a very poor acoustic medium that can hardly sustain significant acoustic pressure. Fourthly, the air bubbles and abrasive particles are strong acoustic scatters. The great population of these scatters in the liquid results in a large effective absorption coefficient that stops the propagation of acoustic wave within a very short distance. Fifthly, only longitudinal acoustic wave (propagating along the direction of vibration) can be supported in liquid. Based on their transverse motion, brush bristles can hardly generate longitudinal acoustic wave with sufficient cleaning power that propagates into inter-dental areas. Finally, the transmission of a wave through an opening is appreciable only when the smallest dimension of the opening is comparable to or larger than the wavelength of the wave. Since the wavelength of acoustic wave of 500 Hz is in the order of meters and the smallest dimension of the typical opening of inter-dental and gingival areas is in the order of millimeters, the acoustic wave is almost totally repelled from inter-dental and gingival areas.

Cavitation is created by much greater high and low pressure in the liquid, and that is the phenomenon on which ultrasound cleaning actually based. Here, the term cavitation refers to the vaporous cavitation rather than the gaseous cavitation that is associated with the dissolved air bubbles. Gaseous cavitation involves much lower acoustic intensity and hardly has any cleaning effect. In vaporous cavitation, small vapor bubbles are generated in the liquid by the low-pressure troughs. When the following high-pressure crests come along, these vapor bubbles implode, i.e., collapse rapidly. The nearby liquid rushes in at high speed to fill the space formerly occupied by the vapor bubble. This action results in a violent local agitation of the liquid, which produces a thorough cleaning effect. Among other conditions, cavitation requires a threshold of acoustic wave intensity of the order of a few watts per square centimeter. Such threshold is far beyond the limit of the combination of the thin layer of loose fluid and brush bristles. Furthermore, the diameter D of the vapor bubble is inversely proportional to the wave frequency f, according to the equation $D=\eta/f$, where $\eta=600$ cm/s. Large bubbles require even more stringent laboratory conditions. In practical conditions, cavitations mainly occur at ultrasonic frequencies, from 20 kHz to 1 MHz. Ordinary electrical toothbrushes, limited as they are by their mechanical systems, do not operate at such high frequencies at all.

In conclusion, the cleaning effect of ordinary electrical toothbrushes derives by and large from the ordinary abrasive brushing action. The corresponding acoustic-wave action is of little significance and there is no cavitation effect. Whatever superior cleaning effect over that of manual toothbrushes derives almost exclusively from the much greater frequency of the bristles motion.

Another group of proposed electrical toothbrushes in the prior art comprises the so-called ultrasonic toothbrushes. The brush heads of the ultrasonic toothbrushes are driven by ultrasonic transducers, rather than by electrical motors. See, for example, U.S. Pat. No. 5,546,624 to Bock (1996), U.S. Pat. No. 5,311,632 to Center (1994), U.S. Pat. No. 4,991,249 to Suroff (1991), and U.S. Pat. No. 4,333,197 to Kuris (1982). The basic idea behind the proposed ultrasonic toothbrushes is to make the brush head vibrate at ultrasonic frequencies, hoping that this could provide superior results to those of ordinary electrical toothbrushes. Unfortunately, the basic physical principles do not support that idea and none of the proposed ultrasonic toothbrush has been successfully produced.

Nonetheless, compared to any mechanical scrubbing mechanism, ultrasounds not only provide superior cleaning results, but also prevent damage to the object being cleaned, provided that appropriate intensity and duration are applied. Ultrasound cleaning can be used for extremely tough jobs such as cleaning a carbonized fuel injector, as well as extremely delicate jobs such as cleaning a semiconductor wafer. A very important property of ultrasound is that it can penetrate into small holes because of short wavelength. Hence, it can clean places that are inaccessible to ordinary mechanical cleaning tools. Because of this property, a mechanical assembly (such as the core of a mechanical watch) can be cleaned by ultrasound without having to be disassembled. So, ultrasound may indeed be an ideal means to clean teeth as a result of these properties, but only if used correctly. Otherwise, ultrasound is not only ineffective, but also hazardous.

Industrial ultrasound cleaning uses frequencies from 20 kHz up to several hundred kHz, and uses power levels from a few watts per gallon (of cleaning solution) up to a few hundred watts per gallon. When the ultrasound power level exceeds the cavitation threshold, millions of vapor bubbles are generated and subsequently implode in the cleaning solution during each wave cycle For an ultrasound of 100 kHz, there are one hundred thousand wave cycles in one second and the diameter of a vapor bubble is about 0.06 mm. These vapor bubbles, like millions of tiny brushes, work simultaneously on the entire surface of the object being cleaned.

Various ultrasound dental cleaning devices have been proposed. Although different in designing details, they all basically derive from other ultrasonic tools, such as ultrasonic drills or scalers, with modified applicators. Examples of the prior-art ultrasound dental cleaning devices include U.S. Pat. No. 6,514,077 to Wilk (2003), U.S. Pat. No. 4,176,454 to Hatter et al. (1979), U.S. Pat. No. 4,148,309 to Reibel (1979), and U.S. Pat. No. 4,071,956 to Andress (1978). Unfortunately, these prior-art designs disregard basic physical principles and safety issues of ultrasound application. In particular, they suffer from the following disadvantages.

1. They do not direct the ultrasound radiation towards the teeth (most of them in fact mainly direct ultrasound radiation towards the throat of the user).
2. The radiation surfaces of the applicators are too far from the teeth.
3. They provide either insufficient ultrasound radiation to the dental surface or excessive ultrasound radiation to other surfaces of the oral cavity.
4. They do not provide uniform ultrasound radiation on the dental surface.
5. Most of them operate with open mouth hence the upper teeth are not effectively cleaned or not cleaned at all.
6. They provide insufficient protection or no protection at all to mouth tissue.
7. They require large amounts of cleaning solution.
8. They are not energy efficient because of the nondiscriminatory radiation.
9. They are difficult to use, especially for self-use.
10. They involve high risk of injury and damage by ultrasound radiation.

In conclusion, despite the improvements of dental hygiene devices over the years, many problems remain either unsolved or their solutions remain unsatisfactory. There is definitely a need for a dental hygiene device that can substantially overcome the aforementioned disadvantages of the prior-art dental cleaning devices and provide overall satisfactory results.

BRIEF SUMMARY OF THE INVENTION

The present invention is an ultrasound oral hygiene and therapeutic device. The fundamental idea of the present invention is to use the combination of an ultrasonic transducer array and a filling means to precisely control the ultrasound radiation on each part of the oral cavity desirable to be treated for cleaning and therapies. As a result, every surface of the oral cavity desirable to be treated, especially the dental surface, including the inter-dental and gingival areas, is cleaned and treated for therapy simultaneously, uniformly, and effectively with optimal amount of ultrasound radiation, while every part of the oral cavity is protected from overdose of ultrasound radiation. The present invention overcomes all of the aforementioned disadvantages of prior-art dental cleaning devices, including manual toothbrushes, ordinary electrical toothbrushes, whole-mouth and multi-head toothbrushes, ultrasonic toothbrushes, and ultrasound dental cleaning devices. In summary, the ultrasound oral hygiene and therapeutic device of the present invention provides the following advantages.

1. It provides far superior cleaning results.
2. It delivers the ultrasound radiation only to the parts of the oral cavity desirable to be treated.
3. It confines the ultrasound radiation to a limited ultrasound action zone surrounding the surfaces desirable to be treated.
4. It controls precisely the desired amount of ultrasound radiation on each part of the oral cavity desirable to be treated.
5. It provides uniform ultrasound radiation to each part of the oral cavity desirable to be treated.
6. It eliminates the hard-to-reach areas of the prior-art dental cleaning devices.
7. It cleans inter-dental and gingival areas, thus eliminating the need for supplemental cleaning devices.
8. It protects all tissues from any possible overdose of ultrasound radiation hence is safe to use.
9. It treats all parts of the oral cavity desirable to be treated simultaneously, hence requires much less time and labor on the part of the user.
10. It requires no control from the user as opposed to the prior-art dental cleaning devices, such as maintaining the right pressure, right duration, right direction of motion, and working around the entire dental surface.
11. It provides consistent results to every user at every time.
12. It provides additional therapeutic benefits, such as massaging the gums, stimulating blood circulation, promoting tissue (bone) growth, increasing absorption, hence, potency of chemical agents and medicines (such as bleaching agents, fluoride, etc.).

13. It contains no moving mechanical part in the conventional sense, hence, is highly durable.

14. It has no parts that are easily worn-out and need to be replaced regularly.

15. It is energy efficient.

16. It produces no noise.

17. It uses only a small amount of cleaning solution.

18. It requires hardly any dexterity on the part of the user hence is easy to use.

In fact, all that a user has to do is to put on the oral hygiene and therapeutic device of the present invention, push the start button, and wait for the device to finish in a short period of time.

BRIEF DESCRIPTION OF THE SEVERAL VIEWS OF THE DRAWING

In the drawings, closely related figures have the same number but different alphabetic suffixes.

FIG. 2-B is the elevated view of the skeleton of the mouthpiece of the oral hygiene and therapeutic device of the present invention.

FIG. 5-B shows a cordless version of the oral hygiene and therapeutic device of the present invention.

DETAILED DESCRIPTION OF THE INVENTION

Preferred Embodiment

Figure 1:
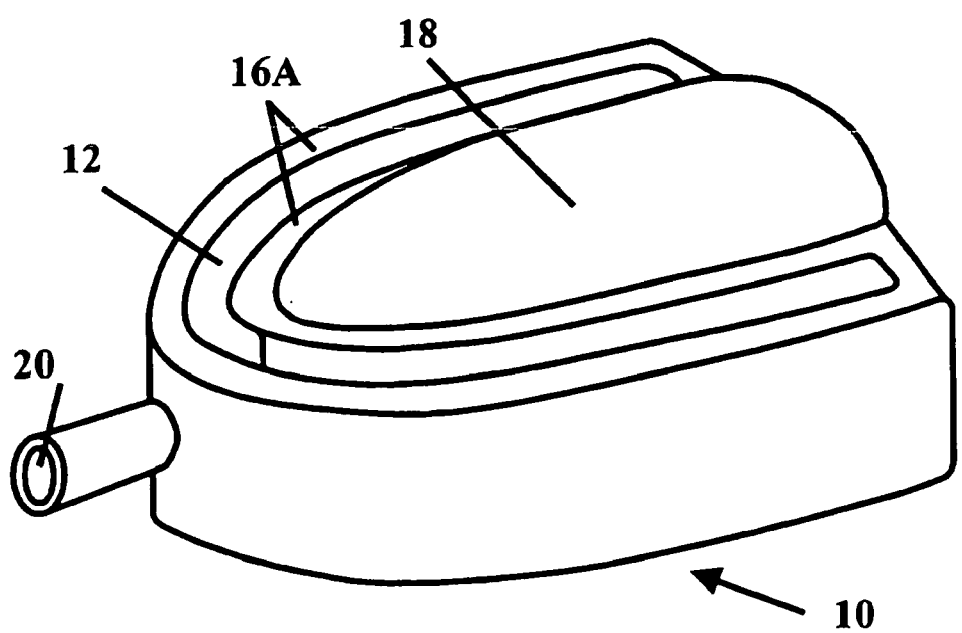
FIG. 1 is an elevated view of the mouthpiece of the oral hygiene and therapeutic device of the present invention.
Figure 5A:
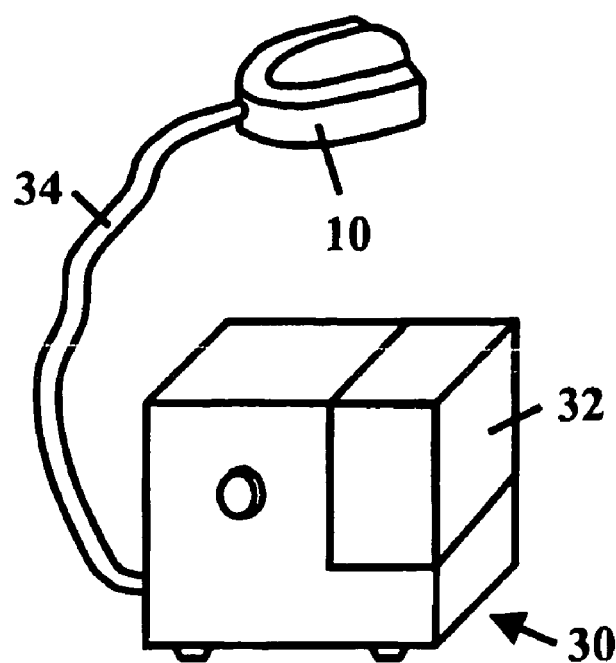
FIG. 5-A shows a wired version of the oral hygiene and therapeutic device of the present invention.
Figure 5B:
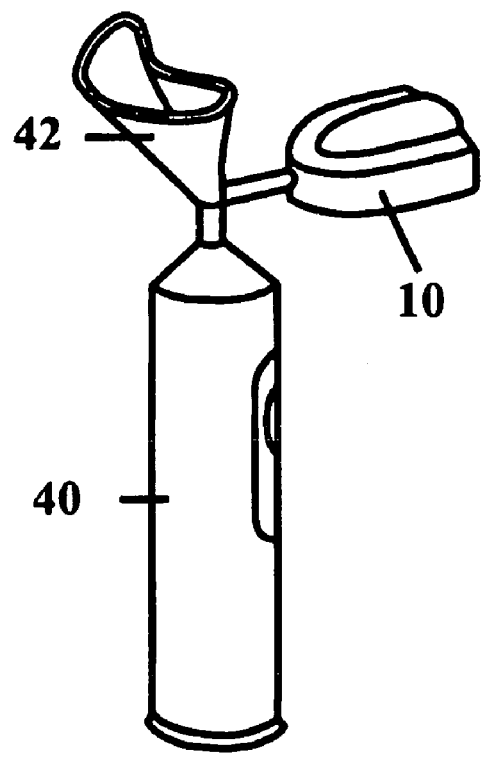

Refer to FIG. 1 for the mouthpiece 10 of the preferred embodiment of the present invention. The mouthpiece may have several different sizes, such as small, medium, and large, each targeting a size group in the general population. It may also be custom fitted for particular individuals if desirable or necessary. The mouthpiece has a soft shell made of rubber or other soft, resilient, and waterproof material. The mouthpiece has a tooth groove 12 for the teeth. The curvature of the tooth groove substantially conforms to the arch of the teeth of an average person in a given size group, but has some additional flexibility, which will be explained in more detail later, to fit each individual user in the given size group. Near the upper edge of the tooth groove, there is an upper gum skirt 16A (its counterpart, the lower gum skirt 16B, is shown in FIG. 5). The gum skirt is a thin layer of soft and resilient material and is considered as an integrated part of the soft shell. Surrounded by the tooth groove is a sealed air pocket 18, which substantially fills up the space between the palate and tongue of the oral cavity. A tubular inlet 20 is located in front of the mouthpiece for passing the electrical wires and the cleaning solution, as it will be explained in more detail later. When the mouthpiece is worn in the user's mouth and the user closes his/her mouth, the device automatically yields so that the upper and lower rows of teeth sink into the tooth groove, and the resilient gum skirts tightly press on and cover the upper and lower gums. The external shape of the soft shell substantially conforms to the oral cavity of an average person in the given size group, and its flexibility and resilience results in a snug fit to the oral cavity of an individual user in that size group.

Figure 2A:
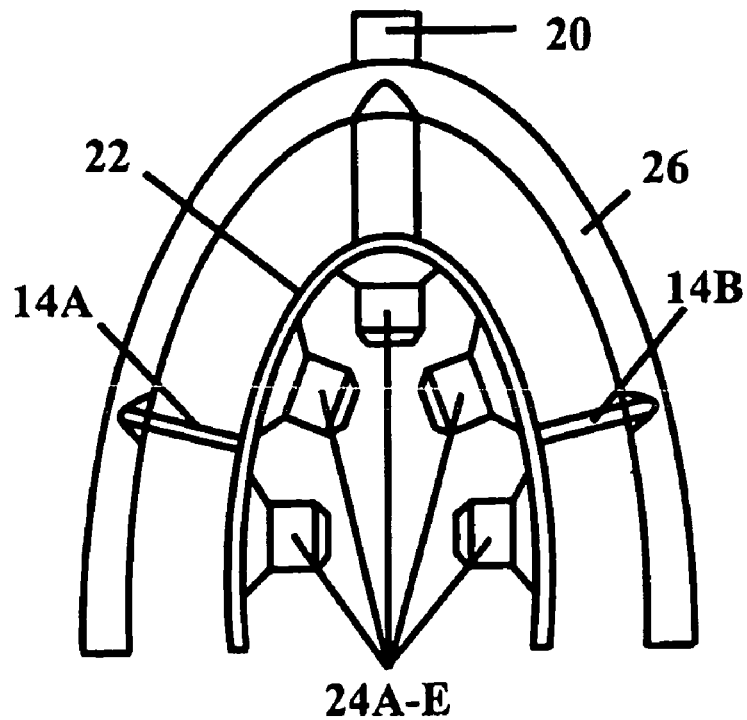
FIG. 2-A is the top view of the skeleton (with soft shell removed) of the mouthpiece of the oral hygiene and therapeutic device of the present invention.
Figure 2B:
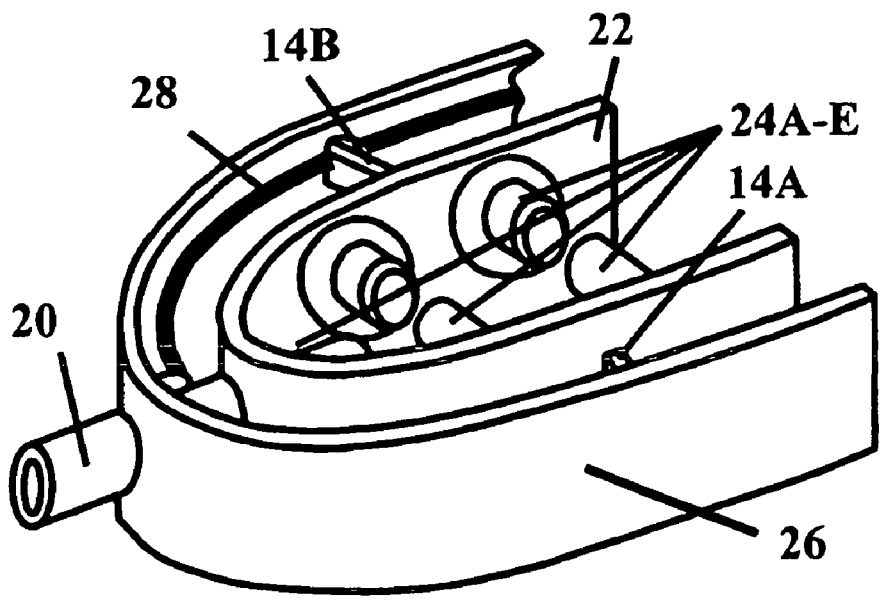

Now refer to FIG. 2-A and FIG. 2-B for the internal structure and elements of the mouthpiece of the preferred embodiment of the present invention. These figures show the skeleton, or the rigid parts of the mouthpiece (with the soft shell removed). The skeleton consists of a radiation plate 22, a reflection plate 26, two spacers, 14A and 14B, and the inlet 20. These parts are jointed together by an acoustically insulating material or by the soft shell, so that they are acoustically decoupled. A number of ultrasonic transducers, 24A to 24E, are head-mounted on the radiation plate.

The spacers, 14A and 14B, not only regulate the distance between the radiation plate and the reflection plate, but also regulate the spacing between the upper and lower rows of teeth, as will be explained in more detail later.

The radiation plate 22 is flexible and resilient, and is made of a material with suitable dimensions and acoustic properties for interfacing the ultrasonic transducers and the cleaning solution. The reflection plate 26 is also flexible and resilient, and is made of a material whose acoustic impedance substantially differs from that of the cleaning solution. The reflection plate 26 has a ridge 28 along its central line and has a number of v-notches to improve its flexibility. The curvatures of the radiation plate and reflection plate conform to the arch of teeth of an average person of a given size group. Since the structure of the skeleton is flexible and resilient, it can fit to the arch of teeth of an individual user of that size group.

The ultrasonic transducers can be any type suitable for radiating into liquid media, such as the common Tonpilz or Janus designs. Resonators may also be used to move the resonant frequency into the desired range. The structure of the radiation plate and the transducer array is somewhat similar to the so-called Isabelle or ring transducer, except that the radiation plate of the present invention is open in the back, rather than closed as a ring. This is important, because radiation towards the throat of the user must be eliminated and the open structure provides the needed flexibility. The transducers are covered by an electrically insulating coating (or each of them has an electrically insulating housing) and are electrically connected in parallel. The (insulated) electrical wires pass through the inlet 20 to the power generator, which will be described later. The inlet 20 has openings in the section between the radiation plate and the reflection plate for the cleaning solution to enter that region.

The soft shell embeds the skeleton and seals the transducers inside its air pocket, exposing only the outer surface of the radiation plate, the inner surface of the reflection plate, the spacers, and the inlet. Since the transducers are air-backed, they only radiate outward through the radiation plate.

Figure 3:
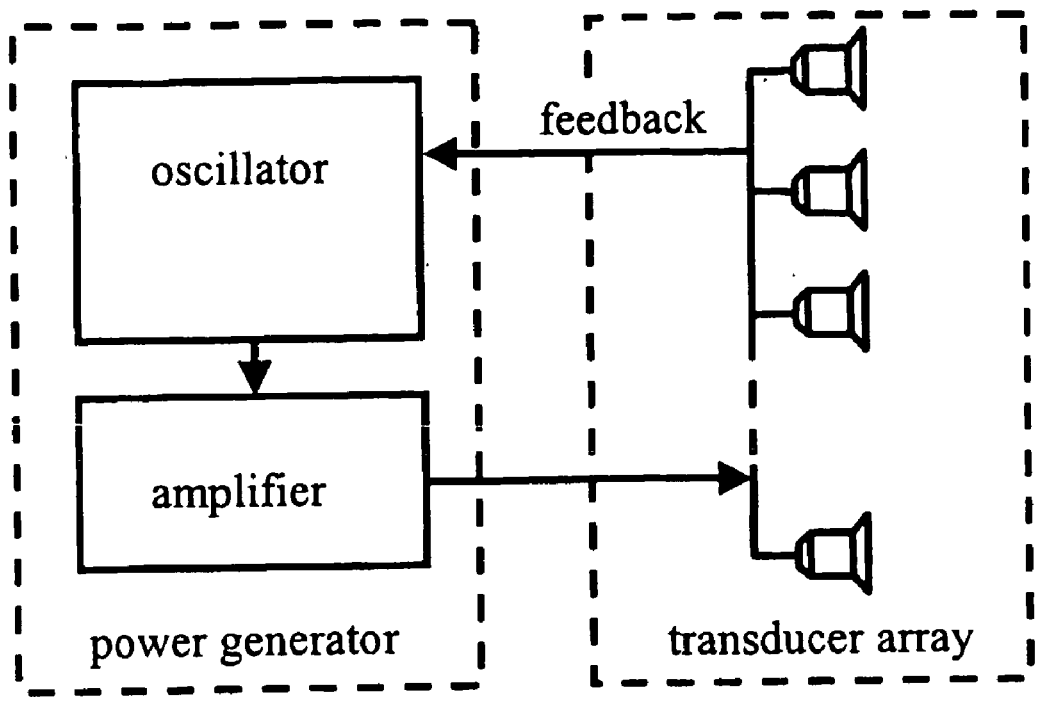
FIG. 3 is the schematic diagram of the power generator of the oral hygiene and therapeutic device of the present invention.

Now refer to FIG. 3 for the schematic diagram of the power generator that drives the transducers. The power generator is powered either by DC electricity or by household AC electricity. The power generator consists of an oscillator that generates a alternating signal, an amplifier that amplifies the alternating signal to the desired voltage and power level, and a feedback control circuit that, according to the feedback signal, dynamically tunes the oscillator to the targeted frequency. The targeted frequency can be, for example, the frequency that makes the load impedance minimal. The feedback control circuit can provide further safety by turning the power off if the load impedance falls out of the designed range due to low level of cleaning solution or electrical failure. Also, a timer is equipped to control the duration of a cleaning session. These kinds of circuits and components are well known in the art.

Figure 4:
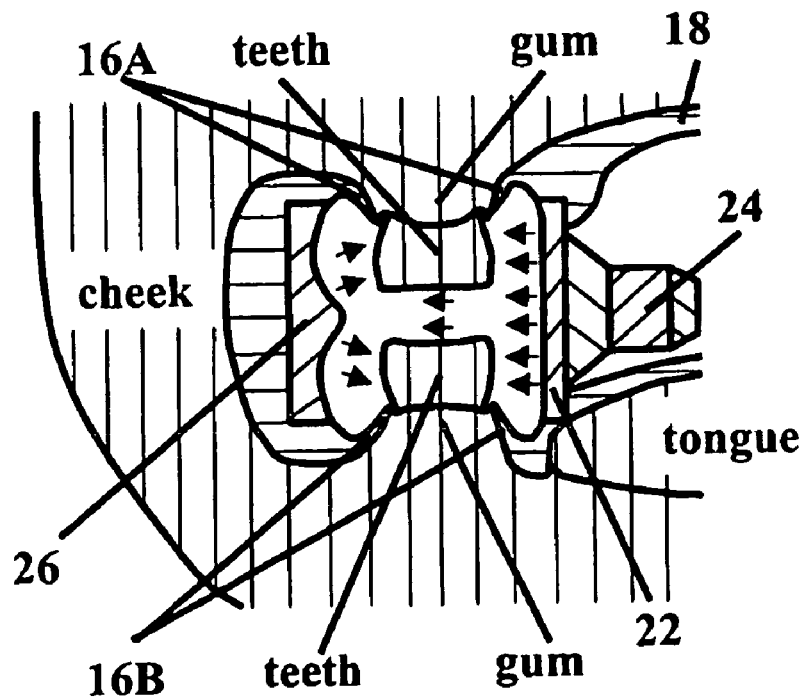
FIG. 4 shows the mouthpiece of the oral hygiene and therapeutic device of the present invention in operation.

Now refer to FIG. 4 for the operation of the mouthpiece of the preferred embodiment of the present invention. FIG. 4 is a sectional view cutting along a plane parallel to the face of the user wearing a mouthpiece, and it shows only half of the oral cavity (the other half is simply a mirror image). In FIG. 4, the vertical shading represents the human tissue, including both soft and hard tissue, while the horizontal shading and oblique shading represent, respectively, the soft shell and the rigid parts of the mouthpiece. When the mouthpiece is worn in the user's mouth, the spacers, 14A and 14B (neither is shown in this figure) separate the upper and lower row of teeth, leaving a gap between them and exposing the chewing surfaces of the teeth. Preferably, the shadow area, i.e., the contact area of the spacers and the teeth, is small. The structure of the mouthpiece also provides a suitable space between the radiation plate and the inner surface (tongue side) of the teeth and a suitable space between the reflection plate and the outer surface (cheek side) of the teeth. As a result, the mouthpiece substantially fills the entire oral cavity, leaving only a limited region surrounding the teeth. This limited region shall be referred as ultrasound action zone. The ultrasound action zone is filled by a cleaning solution and is where the ultrasound radiation is confined. Note that it contains all unoccupied spaces in the tooth groove, including the vacancies between adjacent teeth and that between the teeth and gums. The gum skirts, 16A and 16B, tightly press on and protect the gums.

When the transducers are turned on, the radiation plate 22 radiates ultrasound (indicated by arrows) uniformly into the cleaning solution, towards the inner surface of the teeth and the gap between the upper and lower rows of teeth. The reflection plate 26 splits the incident wave with its center ridge, and reflects the split waves uniformly towards the outer surfaces of the upper and lower rows of teeth. The height of the spacers, which determines the gap between the upper and lower rows of teeth, is selected such that the outer surface of the teeth receives the same amount of ultrasound radiation as the inner surface. The configuration (width, shape, and distance) of the radiation plate and the reflection plate is designed to provide a substantially uniform distribution of the ultrasound intensity on the entire dental surface. Furthermore, the configuration must ensure that waves do not interfere destructively. Because the mouthpiece fills all other spaces of the oral cavity, the cleaning solution is substantially confined within the ultrasound action zone. Even if a small amount of cleaning solution may leak out of the ultrasound action zone due to somewhat imperfect fitting of the mouthpiece in an individual oral cavity, the ultrasound action is always confined within the ultrasound action zone. The ultrasound radiation also penetrates into the spaces between adjacent teeth and the space between the gum and teeth. As a result, the entire dental surface, including all inter-dental and gingival areas, receives uniform ultrasound radiation.

The mouthpiece may be equipped with a storage box whose inner wall is shaped to mimic the oral cavity so the mouthpiece fits in perfectly. Such a storage box can be used for denture cleaning. A user simply puts the mouthpiece and dentures together in the storage box with the denture teeth inside the tooth grove, fills the tooth groove with cleaning solution, and turns on the device.

Rubber blocks may be used for users with missing teeth. A rubber block has substantially the same width and height of a tooth and a thickness slightly greater than the width of the tooth groove so that it can be snugly inserted into the tooth groove in the place of a missing tooth.

The oral hygiene and therapeutic device of the present invention operates at a designed intensity below the biological safety limit. Since only the dental surface receives ultrasound radiation and all other parts of the mouth are protected, relatively high power level can be used, if necessary. When using intensities above the cavitation threshold, the dental device utilizes the cavitation effect. In this case the cleaning solution is preferably continuous (without particles) since vapor bubbles tend to generate at discontinuities. With a continuous cleaning solution, vapor bubbles concentrate at the dental surface. For good cavitation, the cleaning solution should also have a high surface tension, low vapor pressure, and low viscosity. Intensities below the cavitation threshold can also be used. In that case, the cleaning solution may contain small abrasive particles of suitable size and weight such that they resonant with the ultrasound wave. At each cycle, these small particles impinge on or scrub against the dental surface, thus knocking off the deposits. Cleaning solution also contain chemicals and other additives suitable for cleaning and protection (e.g., fluoride). The optimal power level and duration for both cases can be determined by experiment and are built into the design. Low to medium power levels may be suitable for daily use: normal dental cleaning, plaque removing, and periodontal disease prevention. High power levels may be used for occasional treatment, such as removing tartar and tough stains.

FIG. 5-A shows a wired version of the oral hygiene and therapeutic device of the present invention, where the mouthpiece 10 is connected to a station 30 through a flexible cord 34. The station 30 plugs into a household power socket and contains the power generator (shown in FIG. 4), a cleaning solution tank 32, and a water pump (not shown). When the dental device is turned on, the water pump pumps the desired amount of cleaning solution into the ultrasound action zone through an irrigation channel embedded inside the cord 34. Then, the transducers are turned on and the cleaning begins.

FIG. 5-B shows a cordless version of the oral hygiene and therapeutic device of the present invention, where the mouthpiece 10 is connected to a handle 40 with a funnel 42. The handle 40 is the housing for the power generator, a rechargeable battery pack, and a charging circuit (none of which is shown in this figure). When the handle 40 rests on the charging station (not shown), an inductance coil (not shown) in the handle couples to the electromagnetic field produced by the charging station and draws energy to charge the rechargeable battery. A user wears the mouthpiece, closes his/her mouth, feeds a desired amount of cleaning solution through the funnel 42 into the ultrasound action zone, and then turns on the device. The funnel can also be used with the wired version. In that case both the cleaning solution tank and water pump of the station 30 are eliminated.

In both wired and cordless versions, the mouthpiece may be detachable, hence, the station 30 and the handle 40 can be shared by multiple mouthpieces for the entire family. After each use, the user simply detaches the mouthpiece and rinses it with water. Since the cleaning solution is liquid and there is no blocked area in the mouthpiece, the cleaning of mouthpiece should be easy. The user can also use the storage box described earlier for a thorough self-cleaning of the mouthpiece (similar to denture cleaning) if desired.

There are four major factors that affect the cleaning process: mechanical energy, heat, chemistry, and time. The oral hygiene and therapeutic device of the present invention effectively combines all four factors. Ultrasound provides mechanical energy and produces heat. The ultrasound power level and the ultrasound absorption coefficient of the cleaning solution control precisely the amount of heat produced. The cleaning solution contains necessary chemicals for cleaning. The device controls the optimal time for effective and safe ultrasound cleaning. Furthermore, it is known that ultrasound kills bacteria that produce plaque and cause tooth decay and periodontal disease.

Researches have shown that ultrasound also has therapeutic effects, such as stimulating blood circulation, promoting tissue (bone) growth, and increasing the absorption, hence, the potency of chemical agents and medicines (such as bleaching agent, fluoride, etc.). When a person uses the oral hygiene and therapeutic device of the present invention for dental cleaning, he/she benefits from all these therapeutic effects at the same time. The oral hygiene and therapeutic device of the present invention may also be designed, with correspondingly suitable power levels and durations, for more specific therapeutic and other purposes. One example is tooth bleaching, where the bleaching agent now replaces the cleaning solution. Ultrasound enhances the potency of the bleaching agent, hence, the result of bleaching.

Alternative Embodiments

It should be understood that the preferred embodiment described in the preceding section serves only as an example. Based on the fundamental idea and the spirit of the present invention, various alternative embodiments can be designed.

In the preferred embodiment either the radiation plate or the reflection plate is made of one piece. The skeleton may be constructed with a number of units, each consisting of an ultrasonic transducer (or several of them), a shorter radiation plate, and a shorter reflection plate. These units are then hinged or connected by flexible links. Such design further increases the flexibility of the mouthpiece and acoustically separates these units. When each ultrasonic transducer has its won radiation plate, the transducers are mounted on a frame at their nodal points where there is no displacement. In such case the radiation plate may be considered as an integrated part of the transducer (head), or in other words, there is no radiation plates. Furthermore, if the acoustic impedance of the soft shell is substantially different from that of the cleaning solution, the reflection plates can be eliminated as well.

In the preferred embodiment, the mouthpiece has an air pocket for housing the transducers. The air pocket can be filled with a foaming or sponge type material for additional structural integrity and electrical insulation.

Figure 6:
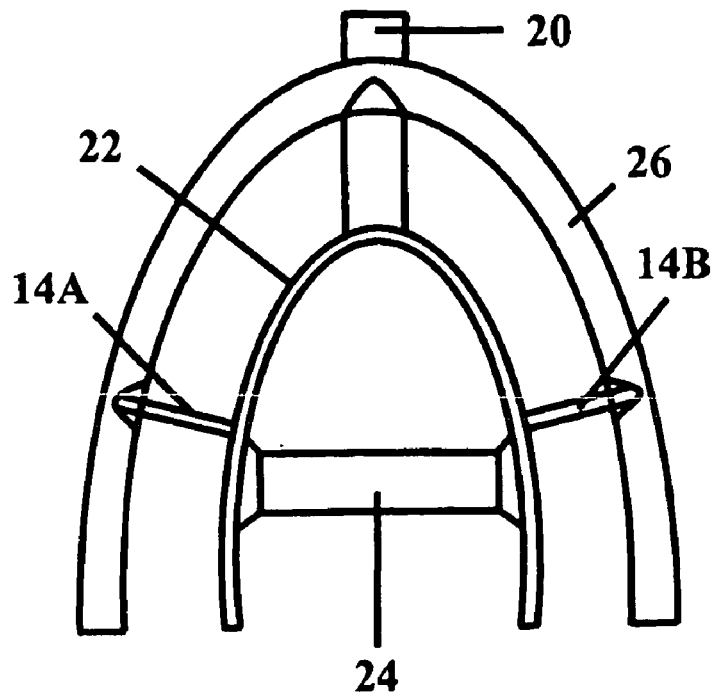
FIG. 6 shows a different embodiment of the skeleton of the mouthpiece of the oral hygiene and therapeutic device of the present invention where only one symmetric ultrasonic transducer is used.
Figure 7:
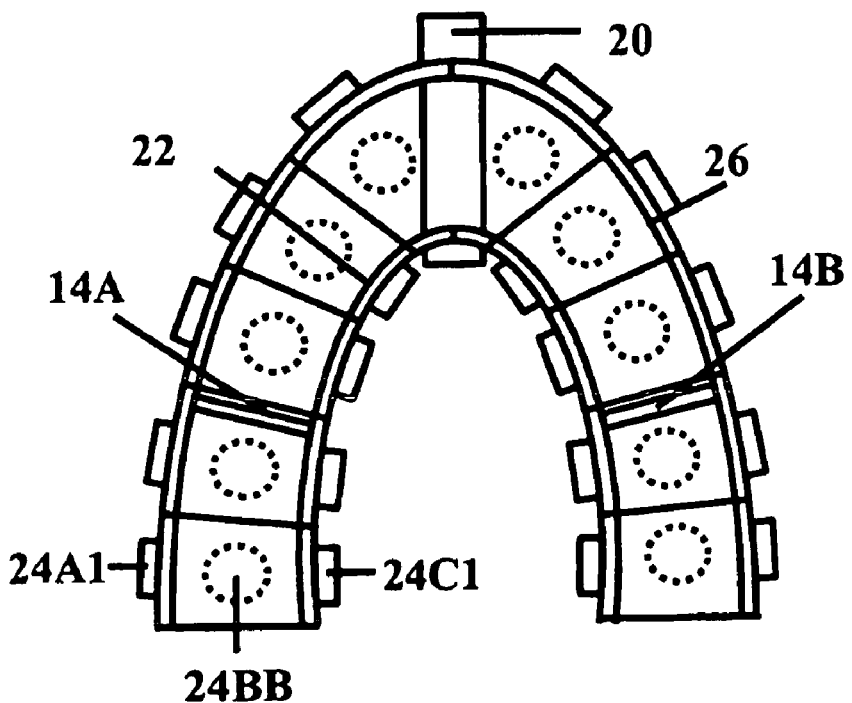
FIG. 7 shows a different embodiment of the skeleton of the mouthpiece of the oral hygiene and therapeutic device of the present invention where many miniature ultrasonic transducers are used.

In the preferred embodiment, five ultrasonic transducers are shown. Different number of ultrasonic transducers may be used. FIG. 6 illustrates one extreme of such designs, where only one ultrasonic transducer 24 with symmetrical design is used. FIG. 7 illustrates the opposite extreme of such designs, where five arrays of miniature ultrasonic transducers, 24-A1, 24-A2 (not shown), 24-B, 24-C1, and 24-C2 (not shown) are used. Transducers in array 24-A1 and 24-A2 radiate inwardly to the outer surfaces of upper and lower teeth, respectively. Transducers in array 24-BB are symmetrically designed and radiate both upwards and downwards into the chewing surfaces of upper and lower teeth, respectively. Transducers in array 24-C1 and 24-C2 radiate outwardly to the inner surfaces of upper and lower teeth, respectively.

In the preferred embodiment the ultrasonic transducers are identical. Different ultrasonic transducers may be used in different locations and they may have their separate radiation plates and reflection plates. In addition, the separation between each pair of the radiation plate and reflection plate may be different at different locations. In this way, desired ultrasound radiation for different sections of the teeth can be controlled even more precisely.

In the preferred embodiment the ultrasonic transducers are connected in parallel, hence, are synchronized and operate for the same time duration. The transducers can be driven individually (best with separate radiation plates and reflection plates) to operate at a different power level, phase, and duration, so that the transducers may be orchestrated to generate any desired ultrasound field.

In the preferred embodiment the ultrasonic transducers are mounted normal to the inner dental surface. The transducers can be mounted at different angles (with their separate radiation plates and reflection plates) in relation to the dental surface if necessary to provide maximum ultrasound power at the dental surface.

In the preferred embodiment the gum skirts cover the gums completely, hence, the gums receive no ultrasound radiation. By varying the length, the thickness of the gum skirts (or by punching holes in them) and the configuration (i.e., the width, position, and curvature) of the radiation and reflection plates, the amount of ultrasound radiation received by the gums can be controlled quite precisely. Desired amount of ultrasound radiation helps to prevent gum disease, stimulate blood circulation, and improve the health of the gums and of the roots of the teeth. Another alternation is that the gum skirts have hook-down edges such that they slightly pull gums away from the teeth, exposing the gingival areas for easier penetration of ultrasound radiation. Such gum skits are especially suitable for users with periodontal disease. They usually have large separation or pockets between their gum and teeth.

In the preferred embodiment two spacers are used. Any suitable number spacers may be used. Or, the inlet may also be used as a spacer in addition of its won functions.

In the preferred embodiment the objective is to clean teeth. Hence, the mouthpiece covers all other surfaces of the oral cavity, except the dental surface, and the ultrasound radiation is delivered to the dental surface only. Without deviating from the fundamental idea and the spirit of the present invention, in general, the configuration can be modified to treat all desired parts of the oral cavity. Each part of the oral cavity can be acoustically exposed to desired amount (including zero amount) ultrasound radiation. This can be achieved by properly configuring the radiation plate, the reflection plate, and the ultrasonic transducers, and by varying the acoustic coverage of the mouthpiece at different areas from complete (thick and full) coverage to partial (thin, partial or with holes) to no coverage. Desired amount ultrasound radiation on other surfaces, for example, the tongue surface and palate surface, can clean these surfaces and kill and remove the bacteria that cause breath odor. So generally speaking, the ultrasound action zone, where the cleaning solution and ultrasound action are confined, is not limited to proximity of dental surface but may include all vacancies in the oral cavity that are deliberately not filled by the filling means.

In the preferred embodiment, the power generator outputs a single-frequency alternating waveform of a predetermined power level for a predetermined duration. More elaborated power generators may allow users to select from a given set of power level and duration combinations, or to adjust the power level and duration independently and continuously. Or users may choose from a variety of programs, each designed for a more specific cleaning or therapy procedure, with a correspondingly specific or time-varying power level. Furthermore, the output of the power generator is not limited to a simple alternating form, but it may be of any other desired waveform, such as pulses or modulated waveforms, for various cleaning effects or therapies. Several different cleaning solutions may also be used for different purposes or at different cleaning steps, if necessary.

In the preferred embodiment, the power generator is external to the mouthpiece. With compact design and integrated circuits, it may be possible to fit some parts or even the entire power generator circuit inside the mouthpiece. One of such embodiment is that the external power generator generates a lower voltage output, and a transformer embedded in the mouthpiece converts the low-voltage power to the required the voltage to drive the transducers.

Conclusion, Ramification, and Scope

The fundamental idea of the present invention is to use the combination of an ultrasonic transducer array and a filling means to precisely control the ultrasound radiation on each part of the oral cavity desirable to be treated for cleaning and therapies. As a result, every surface of the oral cavity desirable to be treated, especially the dental surface, including the inter-dental and gingival areas, is cleaned and treated for therapy simultaneously, uniformly, and effectively with optimal amount of ultrasound radiation, while every part of the oral cavity is protected from overdose of ultrasound radiation.

Since ultrasound cleaning is much more effective than mechanical brushing and the entire dental surface is cleaned simultaneously, the oral hygiene and therapeutic device of the present invention is much more effective and uses much less time than any prior-art dental cleaning device.

Since ultrasound cleaning is much more delicate than mechanical abrasive brushing, the oral hygiene and therapeutic device of the present invention does not damage the dental surface and gums as opposed to prior-art dental cleaning devices.

Since the ultrasound radiation is uniformly distributed on each specific surface, the oral hygiene and therapeutic device of the present invention provides very uniform results.

Since the cleaning solution and the ultrasound radiation penetrate into small vacancies within the ultrasound action zone, the oral hygiene and therapeutic device of the present invention cleans the inter-dental and gingival areas, eliminates the hard-to-reach areas associated with the prior-art dental cleaning devices, and eliminates the need for supplemental cleaning devices such as dental floss and high-pressure water jet.

Since the desired amount of ultrasound radiation is determined by experiment and is built into the design. The oral hygiene and therapeutic device of the present invention thus completely eliminates any control required from the user as opposed to the prior-art dental cleaning devices, such as maintaining the right pressure, using the right motion type or right orientation, distributing the time evenly, etc. Furthermore, the oral hygiene and therapeutic device of the present invention provides consistent result to every user at every time.

Since it has no moving mechanical parts in the conventional sense, i.e., with relatively large movement as in an ordinary electrical toothbrush, the oral hygiene and therapeutic device of the present invention is much more reliable.

Since it has no easily worn-out part that needs to be replaced regularly, the oral hygiene and therapeutic device of the present invention costs less in the long run than the prior-art dental cleaning devices.

Since the system operates at ultrasonic frequencies, the oral hygiene and therapeutic device of the present invention produces no audible noise.

Since the electrical-to-mechanical conversion efficiency of ultrasonic transducers is as high as 80% with good impedance matching, and the ultrasound radiation is confined within a very limited ultrasound action zone, the oral hygiene and therapeutic device of the present invention is much more energy efficient than the prior-art dental cleaning devices. Also, it uses only a small amount of cleaning solution, just enough to fill up the ultrasound action zone.

Since only the surfaces desirable for treatment receive desired amounts of ultrasound radiation, the oral hygiene and therapeutic device of the present invention effectively uses the ultrasound radiation and protects the user from any ultrasound radiation damage.

The oral hygiene and therapeutic device of the present invention is extremely easy to use. Since it treats all surfaces desirable to be treated simultaneously, a user no longer needs to work on the entire dental surface as with manual and electrical toothbrushes. In fact, all that a user has to do is to wear the mouthpiece in the mouth, push the start button, and wait for it to finish shortly.

Given the exemplary embodiments, numerous alternations, substitutions, modifications, and ramifications will become obvious to the skilled in the art. The fundamental idea and spirit of the present invention is not even limited to dental applications, as it can also be applied to other areas of ultrasound treatment of biological objects. The present embodiments therefore should be considered in all respects as illustrative and not restrictive. All alternations, substitutions, modifications, and ramifications that come within the meaning and range of equivalency of the present invention are covered by the scope of the present invention. The scope of the present invention should be determined not by the exemplary embodiments just described, but by the following claims.

What is claimed is:

1. A method for oral cleaning and therapy using ultrasound radiation, comprising the steps of:
    a) providing a plurality of spacers disposed between the upper and lower teeth of a user to separate them with a predetermined separation and expose the chewing surfaces of the teeth;
    b) providing a plurality of ultrasonic transducers disposed inside the oral cavity of the user with their radiation heads pointing to various predetermined targets with predetermined separations from the targets, said ultrasonic transducers having electrically insulating housings;
c) providing a filling means that substantially fills up the oral cavity of the user, leaving a predetermined ultrasound action zone that acoustically exposes the surfaces of the oral cavity desirable to be treated by ultrasound radiation in such a manner that they receive desired amounts of ultrasound radiation;
d) providing a cleaning solution that contains necessary cleaning and therapeutic agents, said cleaning solution filling up said ultrasound action zone;
e) providing a power generator that is electrically connected to and drives said ultrasonic transducers with predetermined waveforms for predetermined durations;
whereby ultrasound radiation produced by said ultrasonic transducers is confined within said ultrasound action zone, whereby each desired part of the oral cavity is cleaned and treated for therapy simultaneously, uniformly, and effectively by precisely predetermined amount of ultrasound radiation, whereby the entire dental surface, including the inter-dental and gingival areas, is cleaned uniformly and effectively.

2. The method of claim 1 wherein a plurality of radiation plates are further provided, said radiation plates constituting the interface between said ultrasonic transducers and said cleaning solution.

3. The method of claim 1 wherein a plurality of reflection plates are further provided, said reflection plates further helping to direct and confine ultrasound radiation.

4. The method of claim 1 wherein said power generator is capable of generating a plurality of different outputs suitable for different cleaning effects and therapies.

5. The method of claim 1 wherein said power generator further comprises a feedback control circuit that detects the operating status of said ultrasonic transducers and dynamically adjusts its outputs accordingly, said power generator shutting itself down if operating error is detected.

6. An ultrasound oral hygiene and therapeutic device, comprising:
   a) a mouthpiece to be worn in the oral cavity of a user, said mouthpiece having a soft, resilient, and waterproof outer surface that substantially conforms to the oral cavity of the user, a tooth groove that confirms to the arch of the teeth of the user, said mouthpiece substantially filling the oral cavity and leaving a predetermined ultrasound action zone that acoustically exposes only the surfaces of the oral cavity desirable to be treated by ultrasound radiation;
   b) a plurality of spacers disposed inside said tooth groove to separate the upper and lower teeth with a predetermined separation, exposing the chewing surfaces of the teeth;
   c) a plurality of ultrasonic transducers with their bodies embedded in said mouthpiece and their radiation heads pointing to the various predetermined targets with predetermined separations from the targets, said ultrasonic transducers having electrically insulating housings;
   d) a cleaning solution that contains necessary cleaning and therapeutic agents, said cleaning solution filling up said ultrasound action zone;
   e) a power generator that is electrically connected to and drives said ultrasonic transducers with predetermined waveforms for predetermined durations;
whereby the ultrasound radiation produced by said ultrasonic transducers is confined inside said ultrasound action zone and is directed to the desirable parts of the oral cavity with precisely controlled amounts for cleaning and therapy, whereby the entire dental surface, including the inter-dental and gingival areas, is cleaned and treated for therapy simultaneously, uniformly, and effectively, whereby said mouthpiece protects all surfaces inside the oral cavity from overdose ultrasound radiation.

7. The device of claim 6 wherein said mouthpiece further comprises a plurality of radiation plates that constitute the interface between said ultrasonic transducers and said cleaning solution.

8. The device of claim 6 wherein said mouthpiece further comprises a plurality of reflection plates that further help to direct and confine ultrasound radiation.

9. The device of claim 6 wherein said mouthpieces have several different sizes, each fitting a particular size group of users.

10. The device of claim 6 further has a funnel for feeding said cleaning solution into said ultrasound action zone.

11. The device of claim 6 wherein said power generator is external to said mouthpiece and said mouthpieces is detachable from said power generator, whereby multiple said mouthpieces can share said power generator.

12. The device of claim 6 wherein said power generator is embedded in said mouthpiece.

13. The device of claim 6 wherein said power generator is divided into a first part and a second part, said first part being embedded in said mouthpiece and said second part being external to said mouthpiece, and said mouthpiece being detachable from said second part, whereby multiple said mouthpieces can share said second part.

14. The device of claim 6 wherein said power generator is capable of generating a plurality of different outputs suitable for different cleaning effects and therapies.

15. The device of claim 6 wherein said power generator further comprises a feedback control circuit that detects the operating status of said ultrasonic transducers and dynamically adjusts its outputs accordingly, said power generator shutting itself down if operating error is detected.

16. An ultrasound oral hygiene and therapeutic device comprising:
   a) a plurality of spacers disposed between the upper and lower teeth of a user, exposing the chewing surface of the teeth and separating the upper and lower teeth with a predetermined separation;
   b) a plurality of ultrasonic transducers disposed inside the oral cavity of the user with their radiation heads pointing at various predetermined targets with predetermined distances from the targets;
   c) a frame with certain flexibility and adjustability that joints said spacers and said ultrasonic transducers, all joints with said spacers and said ultrasonic transducers are acoustically insulated;
   d) a soft and resilient filling means that substantially fills the unoccupied spaces of the oral cavity, leaving only a predetermined ultrasound action zone which acoustically exposes parts of the oral cavity desirable to be treated by ultrasound treatment and enable them to receive desired amounts of ultrasound radiation for cleaning and therapy;
   e) a cleaning solution that contains necessary cleaning and therapeutic agents, said cleaning solution filling up said ultrasound action zone;
   f) a power generator that is electrically connected to and drives said ultrasonic transducers with predetermined waveforms for predetermined durations;

whereby said cleaning solution and the ultrasound radiation produced by said ultrasonic transducers are confined within said ultrasound action zone, whereby each desired part of the oral cavity is treated simultaneously, uniformly, and effectively by precisely predetermined amount of ultrasound radiation for cleaning and therapy, whereby the entire dental surface, including the inter-dental and gingival areas, is cleaned uniformly and effectively.

17. The device of claim 16 a plurality of radiation plates and a plurality of reflection plates are further disposed inside the oral cavity, said radiation plates and said reflection plates further helping to facilitate, direct, and confine the ultrasound radiation produced by said ultrasonic transducers.

18. The device of claim 16 wherein said filling means further comprises gum skirts with hook-down edges, said hook-down edges of said gum skirts slightly pulling the edges of the gums away from the teeth exposing the gingival areas for cleaning and therapies.

19. The device of claim 16 wherein said power generator is capable of generating a plurality of different outputs suitable for different cleaning effects and therapies.

20. The device of claim 16 wherein said power generator further comprises a feedback control circuit that detects the operating status of said ultrasonic transducers and dynamically adjusts its output accordingly, said power generator shutting itself down if operating error is detected.

* * * * *